United States Patent [19]

Earhart et al.

[11] 4,287,074
[45] Sep. 1, 1981

[54] SEC-YLBIPHENYL COMPOSITION AND PROCESS FOR PREPARING THE SAME

[75] Inventors: Harold W. Earhart, Corpus Christi, Tex.; Donald F. Rugen, Wilmington, Del.

[73] Assignee: Sun Oil Company of Pennsylvania, Philadelphia, Pa.

[21] Appl. No.: 144,490

[22] Filed: Apr. 28, 1980

[51] Int. Cl.³ .......................... B01F 1/00; H01B 3/22
[52] U.S. Cl. ..................... 585/6.3; 252/364; 282/27.5; 585/25; 585/459; 585/461
[58] Field of Search .................... 252/63, 364; 585/25; 282/27.5

[56] References Cited

U.S. PATENT DOCUMENTS

| | | |
|---|---|---|
| 2,172,391 | 9/1939 | Krase ..................... 585/25 |
| 2,264,448 | 11/1941 | Smith et al. ............. 252/63 X |
| 2,837,727 | 3/1958 | Cook ..................... 252/63 |
| 3,732,141 | 5/1973 | Brockett et al. .......... 282/27.5 |
| 3,846,331 | 11/1974 | Konishi et al. ........... 252/364 |
| 4,054,937 | 10/1977 | Mandelcorn et al. ....... 361/319 |
| 4,071,469 | 1/1978 | Vincent et al. ........... 252/364 |
| 4,085,949 | 4/1978 | Asao et al. .............. 282/27.5 |
| 4,118,335 | 10/1978 | Krause et al. ............ 252/299 |
| 4,119,555 | 10/1978 | Jay ...................... 252/66 |
| 4,177,156 | 12/1979 | Jay ...................... 252/66 |

FOREIGN PATENT DOCUMENTS 2142173 3/1972 Fed. Rep. of Germany.

OTHER PUBLICATIONS

Zavgorodnil et al., "Alkylation of Biphenyl With Pseudobytylene in the Presence of $BF_3H_3PO_4$ Catalyst," Proceedings of the Academy of Science of the USSR, pp. 9-11, 1958.

Primary Examiner—P. E. Willis, Jr.
Attorney, Agent, or Firm—J. Edward Hess; Donald R. Johnson; Paul Lipsitz

[57] ABSTRACT

A water-white, essentially odorless liquid useful as a dieletric oil and as a dye solvent, particularly for a carbonless paper solvent, consisting essentially of about 82% to about 88% by weight of mono-sec-butylbiphenyl and about 12% to about 18% of di-sec-butylbiphenyl prepared by reacting highly pure 1-butene or 2-butene with biphenyl at a mol ratio of butene to biphenyl of from about 0.5 to about 0.9 and at a temperature of about 250° F. to about 475° F. in the presence of an aluminum chloride catalyst, distilling the reaction product under vacuum to remove unreacted biphenyl and distilling off the product mixture at a temperature between about 370° F. and about 440° F. at 30 mm Hg. pressure or the equivalent thereof.

6 Claims, 2 Drawing Figures

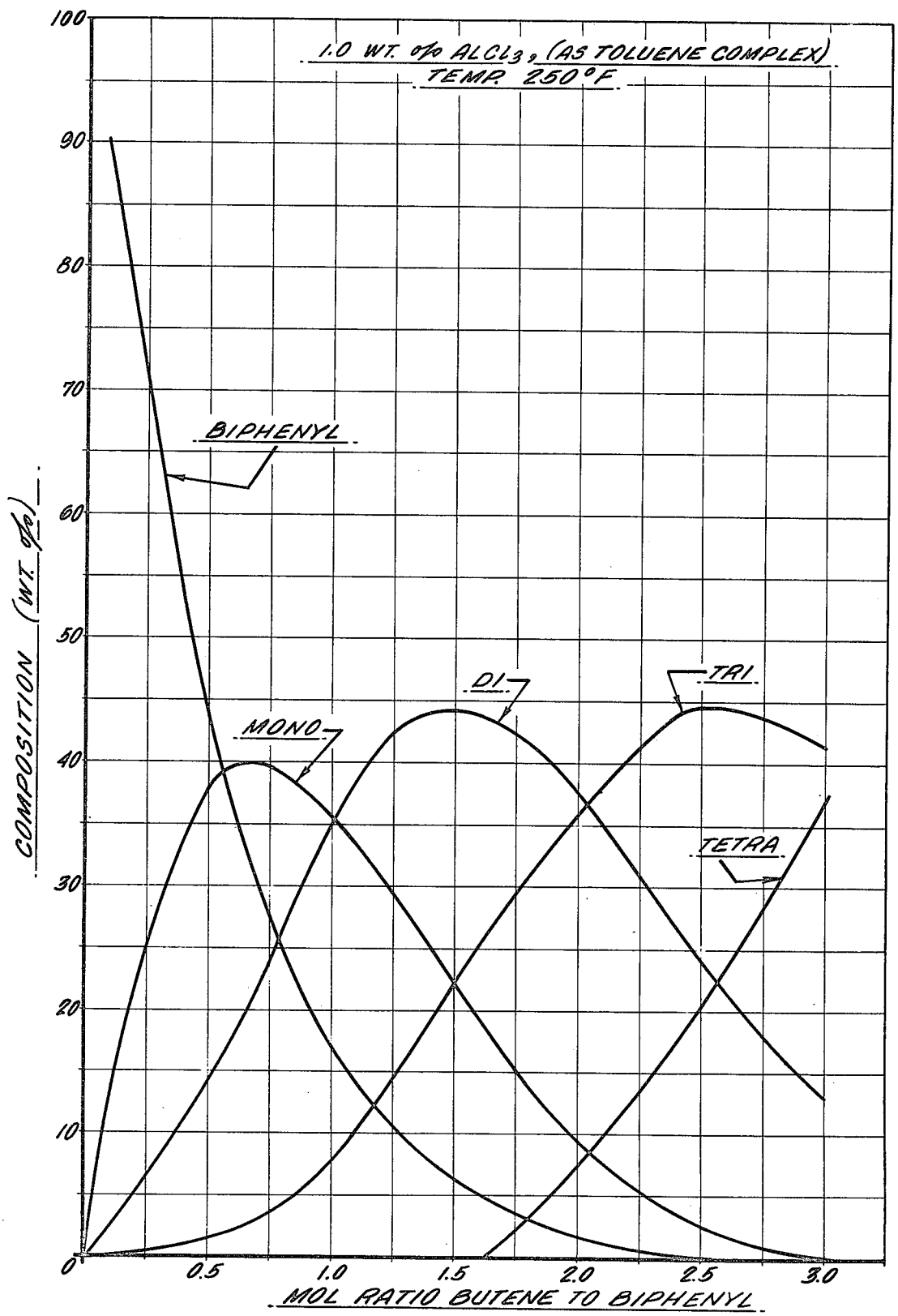

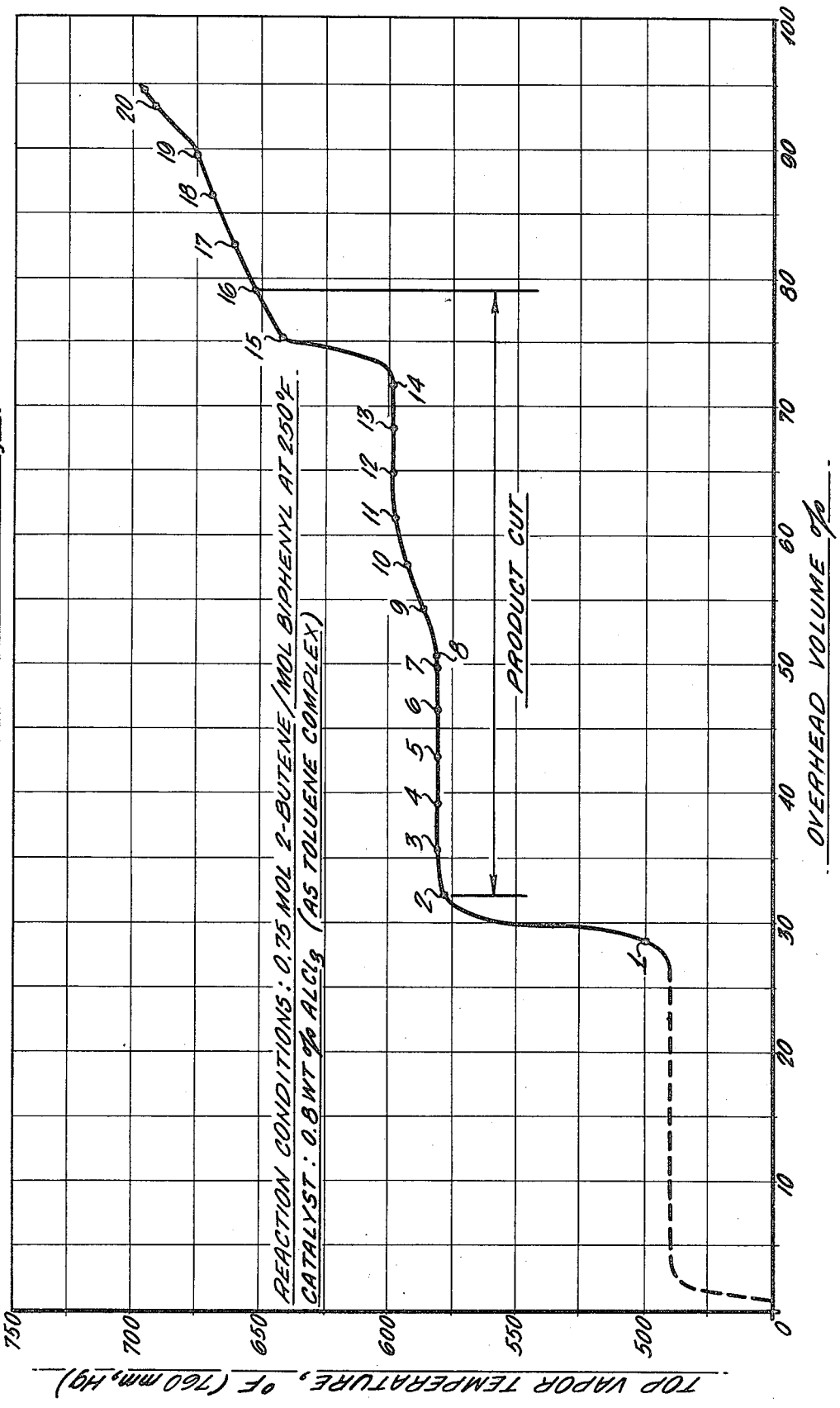

SEC-YLBIPHENYL COMPOSITION AND PROCESS FOR PREPARING THE SAME

It is known in the art that alkylbiphenyl compounds are useful as dielectric materials. For Example, U.S. Pat. No. 2,172,391, which discloses the alkylation of diphenyl, suggests that ethylated diphenyl may be so used. This reference also points out, however, that alkylation of diphenyl with hydrocarbon of molecular weight above ethylene or propylene gives more viscous products which form waxlike crystals on standing. U.S. Pat. No. 2,837,724 discloses the preparation of t-butyl diphenyl and other tertiary alkyl diphenyls for use as a dielectric liquid for transformers. However, 4-t-butyl diphenyl is a solid at room temperature (M.P. 50°–51.5° C.) and its use as a dielectric liquid or as a carbonless paper solvent is impractical as it would be limited to use at elevated temperatures. This problem appears to be recognized in the disclosure of U.S. Pat. No. 4,119,555 relating to use as a dielectric liquid in transformers of a mixture of 30 to 80% by weight of a polychlorobenzene (tri- and tetra-chlorobenzenes) with mono- or polyalkylbiphenyls or terphenyls. The disclosure points out that for use at low temperatures the dielectric must remain liquid with sufficient fluidity and not give rise to deposition of crystals which are apt to block or clog pipelines and pumps which circulate the transformer fluid in certain types of apparatus. The disclosure then states that depending on the physical state at low temperature, the alkyldiphenyls to be used with the polychlorobenzenes can be employed in the pure state or as mixtures of isomers and/or of products with different degrees of alkylation obtained in the course of their preparation. Among a large number of alkylbiphenyls to be used with the polychlorobenzenes are the various butyl isomers including 3-sec-butyl biphenyl, 4-sec-butylbiphenyl, and 4,4'-di-sec-butyl biphenyl, but the thrust of the disclosure is the need to use a mixture of the polychlorobenzenes and alkylated bi- or terphenyl. An earlier issued patent, U.S. Pat. No. 4,054,937, also discloses the use as a capacitor fluid a mixture of mono- and di-alkylated biphenyl where the alkyl group is $C_2$ to $C_4$ and where the fluid comprises 80 to 99% by weight of the monoalkylated biphenyl and 1 to about 20% of the dialkylated biphenyl. The preferred species are normal alkyl and isopropyl. Alkyl groups above butyl are said to have higher pour points and may not be acceptable.

The alkylation of biphenyl with butene is also known in the art to give mixtures of mono- and poly-butyldiphenyls. Zavgorodnil et al (Proceedings of the Academy of Science of the U.S.S.R. pages 9–11, 1958) discusses the alkylation at 50°–100° C. (120°–210° F.) of diphenyl with 2-butene in a carbon tetrachloride solvent system using a $BF_3.H_3PO_4$ catalyst at diphenyl to butene to catalyst ratios of 14:1:0.2–0.3. At temperatures of 70° C. (158° F.) and higher, the authors indicate that the process is accompanied by isomerization of the 2-butene to isobutylene which leads to the formation of a mixture of p-sec-butylbiphenyl and p-tertbutylbiphenyl. Since, as pointed out above, the t-butylbiphenyl isomers are solids at room temperature they are not operable as dielectric oils and their presence in such oils leads to crystallization at reduced temperatures, thereby destroying the utility of the oil.

It is also known in the art that alkylated biphenyls are useful as a dye solvent for carbonless paper (see, for example U.S. Pat. No. 4,085,949). U.S. Pat. No. 3,627,581 discloses isopropylbiphenyl and U.S. Pat. No. 3,732,141 shows mono-isopropylbiphenyl for this purpose. A mixture of phenylnaphthyl methanes and $C_1$ to $C_6$ alkyl biphenyls is disclosed as a dye solvent in U.S. Pat. No. 3,846,331.

It has now been found that a particular mixture of a specific butylated diphenyl can readily be obtained without the contaminating t-butyl isomer and that the mixture has properties making it of particular value as a dielectric liquid and as a carbonless paper solvent. Such material is a water-white liquid with a pleasant odor consisting essentially of about 82% to 88% (preferably 85%) by weight of mono-sec-butylbiphenyl and about 12% to about 18% (preferably 15%) by weight of di-sec-butyl biphenyl. This mixture is readily obtained by alkylation of diphenyl with a highly pure 1-butene or 2-butene or their admixture at a mole ratio of butene to biphenyl of from about 0.5 to about 0.9 (i.e. a biphenyl to butene ratio of 2:1 to 1.1:1) at a temperature of at least about 250° F. up to about 475° F. in the presence of an aluminum chloride catalyst, and vacuum distilling off the alkylation product at a temperature between about 370° F. and about 440° F. at 30 mm Hg of pressure. It is unexpected in view of the Zavgorodnil et al article discussed above that no t-butylbiphenyl isomer is formed at the relatively high temperatures used in the process of the invention. While it is not known why the t-butylbiphenyl isomer is not formed it may be due to the use of the $AlCl_3$ catalyst system employed rather than the $BF_3.H_3PO_4$—solvent system of the reference. It is necessary to use a temperature above the 158° F. temperature of the reference in order to achieve a practical and commercially efficient process. Operations at temperatures below about 250° F. would require large scale and expensive heat exchangers to remove the heat of reaction. By operating at the higher temperature, however, under applicant's conditions which avoid formation of the t-butyl isomer, a practical commercial process is achieved.

As indicated either 1-butene or 2-butene or their admixture in any proportion may be used as the olefin for alkylation since they both give the same product. The butene used, however, must be of high purity because other olefins, even other $C_4$-olefins, drastically alter the properties of the alkylate product. Accordingly, the olefin used must have a purity of at least about 98% of 1- and/or 2-butene.

The catalyst used, as indicated is aluminum chloride. However, it is preferred to use this catalyst as a complex made from $AlCl_3$, toluene, and methyl chloride by adding the $AlCl_3$ (500 parts by weight) to the dry toluene (100 gallons) and then adding the methyl chloride (9 gallons) with agitation. The catalyst complex is a clear, yellow, low viscosity liquid which must be protected from moisture before use. The amount of catalyst used is not critical, but the catalyst complex is preferably used at 0.5 to about 1%, most preferably at a level of 45 gallons of complex per 2500 gallons of biphenyl which corresponds to 0.8 wt. % of solid $AlCl_3$ based on biphenyl. The complex composition is approximately 25–30 wt % $AlCl_3$, 50–60% toluene and 5–10 HCl, the latter derived from the added $CH_3Cl$.

The butene to biphenyl ratio of between about 0.5 and 0.9 is another important parameter in order to obtain the desired product. In order to obtain a product with the preferred amount of 15% di-sec-butyl biphenyl and with a minimum of tri-sec-butyl product, the ratio should be at about 0.75. A butene to biphenyl mol ratio of 0.5 can be used to obtain the desired product but less total product will result per batch. A 0.9 mol ratio can also be used but in such case, less of the sec butyl biphenyl can be used in the final product. Commerical practice dictates that a mol ratio of 0.75 is about optimum. FIG. 1 illustrates the relationship between mole ratio of reactants and the amounts of the various secbutylbiphenyl isomers obtained. It is of interest to note that at the mole ratio used in the process, the amount of tri-sec-butylbipheny isomer is very low and no tetraisomer is present at all.

The rate of addition of the butene to the biphenyl is not critical, but the presence of large amounts of unreacted butene in the reaction mass should be avoided in order to prevent the formation of butene polymers.

In carrying out the alkylation the preferred procedure is to pump the catalyst complex into the molten biphenyl with agitation at about 160° F. The butene or butenes are then added at a rate which allows a maximum temperature of about 250° F. to be held in the reactor. The mono- and di-sec-butyl biphenyl isomers, once formed, are very stable to further heating under conditions which might be expected to produce undesirable by-products. Alkylation in plant equipment is usually completed over a period of from about 3 to about 6 hours.

Upon completion of the addition of the butene, the agitation is stopped and the entire reactor contents (catalyst plus hydrocarbon) are pumped to a hydrolyzer where they are contacted with 20 volume % of 20° Be.NaOH solution at 275°–300° F. for at least 1 hour, preferably 3 hours, followed by a water-wash until neutral. The alkylate is now ready for vacuum distillation.

The principal components of the alkylate at this point are unreacted biphenyl (b.p. 493° F.), mono sec-butyl biphenyl (b.p. 576°–598° F.), di sec-butyl biphenyl (b.p. 598°–691° F.), and higher boiling tri-alkylated biphenyls (bottoms).

Following removal of unreacted biphenyl at 296°–340° F. the desired product, containing from about 82% to about 88% mono and from about 14% to about 18% di sec-butyl biphenyl, is obtained from a vacuum distillation, typically at 30 mm Hg. by taking cuts, preferably from cuts 2 through 16, (b.p. 370°–440° F.) using a 40 plate Heli-Grid column or its equivalent at 20:1 reflux ratio as shown in FIG. 2 where the ordinate temperature values have been converted to the corresponding values at 760 mm Hg. In general, cuts over a range from about 370° to about 440° F. at 30 mm Hg are useful. It will be understood that, as known in the art, equivalent pressure—temperature relationships may be used for the distillation. The product is a water-white, liquid with the physical properties as listed in Table I. The product is essentially free of odor, but any odor that can be detected is pleasant. This low odor characteristic is a particularly desirable property when the product is used as a dye solvent for carbonless paper products and makes the liquid product of the invention superior to a mixture of 85% monoisopropylbiphenyl and 15% diisopropyldiphenyl which has been used heretofore for such purpose.

An unexpected and highly desirable property of the liquid product of the invention is its viscosity, which is an important parameter for electrical oils and for dye solvents for carbonless paper products. The lower molecular weight homologue; i.e. the isopropyl biphenyl, has a suitable viscosity for these use applications, but any significant increase in viscosity would be detrimental. Because, the products of this invention are higher homologes and have a higher molecular weight they would be expected to have a significantly higher viscosity and this is, in fact, the case with the t-butyl compounds, which, as pointed out above are viscous liquids or solids. Surprisingly, however, the viscosity of the liquid products of this invention are not significantly above that for the lower homologue and this is shown in the following Table II:

TABLE I

TYPICAL PRODUCT PROPERTIES

| | Properties |
|---|---|
| Composition | |
| Total Aromatics, Wt. % | 99.0 |
| Mono sec-Butyl Biphenyls, Wt. % | 81–87 |
| Di sec-Butyl Biphenyls, Wt. % | 12–18 |
| Total Sulfur, PPM | nil |
| Total Halogens, PPM | nil |
| Volatility | |
| Engler Distillation, °F. (ASTM D-86) | — |
| IBP | 578 |
| End Point | 610 |
| Flash Point, COC, °F. | 315 |
| General | |
| Gravity | 13.9 |
| Specific Gravity, 60/60 ° F. | 0.9763 |
| Color, Saybolt | +22 |
| Acidity, TAN, mg./g. KOH | nil |
| Odor | Pleasant (essentially odorless) Aromatic |
| Viscosity, SUS @ 100° F. | 49.1 |
| RI, $n_d^{20}$ | 1.573 |
| Pour Point, °F. | $<-50$ |
| KB | 64 |

TABLE II

| Saybolt Viscosity Values (SUS C 100° F.) | |
|---|---|
| Isopropylbiphenyls 85/15 Mono/Di | Sec.-Butylbiphenyls 85/15 Mono/Di |
| 43.0 $\neq$ 1.5 | 49.1 $\neq$ 1.5 |

EXAMPLE

Following the details outlined above, 20,000 pounds (2,500 gallons) of biphenyl was alkylated at 250° F. with 5,190 lbs (1,050 gallons) of 1-butene (mol ratio of butene:biphenyl=0.75) using 45 gallons of an AlCl$_3$.Toluene.CH$_3$Cl complex catalyst which corresponds to 0.8 wt % of solid AlCl$_3$ based on biphenyl. After accumulating cuts distilling at 370° F.–440° F., (at 30 mm Hg) the product contained 85% by weight of the mono-sec-butylbiphenyl and 15% of di-sec-butylbiphenyl as determined by gas chromatography. The colorless product had a Saybolt viscosity (SUS C 100° F.) of 49.1, was essentially free of odor and when evaluated as a carbonless paper solvent for the dye was found to be quite satisfactory for commerical use. The product had the electrical properties shown in Table III and was also commercially acceptable as the dielectric oil in an electrical capacitor wherein the paper spacer was impregnated with the product.

TABLE III

| Electrical Properties of 85/15 Mono/Di Sec-Butylbiphenyl | |
| --- | --- |
| Dielectric Constant @ 100° C. | 2.5 (ASTM D-924) |
| Power Factor @ 100° C. | 0.45% (ASTM D-924) |
| Dielectric Strength | 66.0 KV (ASTM D-877) |

The liquid composition of the invention is also advantageous in that it has very favorable biological properties; e.g. ready biodegradability and low toxicity as shown by the tests summarized in Table IV.

TABLE IV
BIOLOGICAL TEST DATA OF 85/15 MONO/DI SEC BUTYLBIPHENYL

Biodegradation:

Test Compound biodegraded by tenth day;
Skin irritation (rabbits): The test material is not an irritant (by definition). Two animals had severe skin reactions, but at 14 days, all sites were normal or nearly normal.
Acute dermal toxicity (rabbits): The test substance is considered to be a relatively mild skin irritant.
Eye irritation (rabbits): Based on the results of unwashed eyes, the irritation potential of the test material is undeterminate (2 out of 9 had eye redness, etc.). Based on the results of washed eyes, no animals had any redness, etc.
Oral toxicity (rats): LD/50 is greater than 5.0 g/kg. The test material is not considered to be toxic.
Inhalation (rats): No mortality. Within two hours of exposure rats were eating and drinking; all animals gained weight. No abnormalities of internal organs.
Ames test: Material did not demonstrate genetic activity in any of the assays and was considered non-mutagenic under the tested conditions.

The invention claimed is:

1. A water-white, essentially odorless liquid composition useful as a dielectric oil and as a dye solvent, consisting essentially of about 82% to about 88% by weight of mono-sec-butylbiphenyl and about 12% to about 18% of di-secbutylbiphenyl.

2. The composition of claim 1 consisting essentially of about 85% of mono-sec-butyl biphenyl and about 15% of di-sec-butyl biphenyl.

3. A process for preparing a water-white, essentially odorless liquid product useful as a dielectric oil and as a dye solvent, consisting essentially of about 82% to about 88% by weight of mono-sec-butylbiphenyl and about 12% to about 18% of di-sec-butylbiphenyl which comprises reacting highly pure 1-butene or 2-butene with biphenyl at a mol ratio of butene to biphenyl of from about 0.5 to about 0.9 and at a temperature between about 250° and about 475° F. in the presence of an aluminum chloride catalyst, distilling the reaction product under vacuum to remove unreacted biphenyl and thereafter distilling off the liquid product mixture at a temperature between about 370° F. and about 440° F. at 300 mm Hg. pressure or the equivalent thereof.

4. The process of claim 3 wherein the ratio of butene to biphenyl is about 0.75 and the liquid product is distilled over a temperature range of from about 370° F. to about 437° F. at 30 mm Hg.

5. The process of claim 4 wherein the catalyst used is a complex of AlCl$_3$ with toluene and methyl chloride.

6. A process for preparing a water-white, essentially odorless liquid product useful as a dielectric oil and as a dye solvent, consisting essentially of about 85% by weight of mono-sec-butylbiphenyl and about 15% of de-secbutylbiphenyl prepared which comprises reacting highly pure 1-butene or 2-butene, or their admixture with biphenyl at a mol ratio of butene to biphenyl of from about 0.75 and at a temperature of about 250° F. in the presence of an aluminum chloride complex catalyst, distilling the reaction product under vacuum at a temperature between about 296° and 340° F. to remove unreacted biphenyl and thereafter distilling off the liquid product mixture at a temperature between about 370° and about 440° F. at about 30 mm Hg pressure.

* * * * *

UNITED STATES PATENT OFFICE
CERTIFICATE OF CORRECTION

PATENT NO. : 4,287,074
DATED : September 1, 1981
INVENTOR(S) : Harold W. Earhart and Donald F. Rugen It is certified that error appears in the above-identified patent and that said Letters Patent are hereby corrected as shown below:

In the title; Change "SEC-YLBIPHENYL" to ---SEC-BUTYLBIPHENYL---.

In the Abstract, line 2, change "dieletric" to ---dielectric---.

Signed and Sealed this

Third Day of November 1981

[SEAL]

Attest:

GERALD J. MOSSINGHOFF

Attesting Officer     Commissioner of Patents and Trademarks